(12) United States Patent
Belmar et al.

(10) Patent No.: US 7,674,472 B2
(45) Date of Patent: *Mar. 9, 2010

(54) METHOD FOR PREPARING A COSMETIC COMPOSITION AND COSMETIC COMPOSITION PREPARED BY THIS METHOD

(75) Inventors: Maria Teresa Belmar, Bedford (GB); Alexander Lips, Edgewater, NJ (US); Iain Young, Bedford (GB); Shiping Zhu, Bedford (GB)

(73) Assignee: Conopco, Inc., Edgewater, NJ (US)

( * ) Notice: Subject to any disclaimer, the term of this patent is extended or adjusted under 35 U.S.C. 154(b) by 963 days.

This patent is subject to a terminal disclaimer.

(21) Appl. No.: 10/515,371

(22) PCT Filed: Apr. 25, 2003

(86) PCT No.: PCT/EP03/04366

§ 371 (c)(1),
(2), (4) Date: Dec. 12, 2005

(87) PCT Pub. No.: WO03/097003

PCT Pub. Date: Nov. 27, 2003

(65) Prior Publication Data

US 2006/0093569 A1   May 4, 2006

(30) Foreign Application Priority Data

May 22, 2002   (EP) .................................. 02253621

(51) Int. Cl.
*A61K 7/48* (2006.01)
*A61K 8/36* (2006.01)

(52) U.S. Cl. .................. 424/401; 424/70.22; 424/70.31

(58) Field of Classification Search ........................ None
See application file for complete search history.

(56) References Cited

U.S. PATENT DOCUMENTS

| | | | |
|---|---|---|---|
| 1,500,276 A | 7/1924 | Schneible | |
| 2,268,642 A | 1/1942 | Carter | |
| 2,800,398 A | 7/1957 | Morrison | |
| 3,793,214 A | 2/1974 | O'Neil et al. | |
| 4,258,063 A | 3/1981 | Chun et al. | |
| 4,344,446 A | 8/1982 | Ehrhardt | |
| 4,753,747 A | 6/1988 | Clark et al. | |
| 5,174,992 A | 12/1992 | Lindauer et al. | |
| 5,384,115 A | 1/1995 | Bissett et al. | |
| 5,500,155 A | 3/1996 | Weuthen et al. | |
| 5,607,666 A | 3/1997 | Masson et al. | |
| 5,958,431 A | 9/1999 | Boiteux et al. | |
| 6,045,254 A | 4/2000 | Inbar et al. | |
| 6,221,346 B1 | 4/2001 | Streels | |
| 6,221,364 B1 | 4/2001 | Pavelka, Jr. et al. | |
| 6,576,228 B1 | 6/2003 | Crookham et al. | |
| 6,630,432 B2 | 10/2003 | Farrell et al. | |
| 2001/0014343 A1 | 8/2001 | Harbeck | |
| 2005/0002971 A1 | 1/2005 | Belmar et al. | |
| 2005/0013837 A1 | 1/2005 | Belmar et al. | |
| 2005/0019351 A1 | 1/2005 | Belmar et al. | |
| 2006/0093569 A1 | 5/2006 | Belmar et al. | |
| 2006/0251605 A1 | 11/2006 | Belmar et al. | |
| 2007/0104673 A1 | 5/2007 | Belmar et al. | |

FOREIGN PATENT DOCUMENTS

| | | |
|---|---|---|
| DE | 33 04 897 | 7/1983 |
| DE | 33 06 043 | 7/1983 |
| DE | 37 24 900 | 3/1988 |
| DE | 199 27 172 | 8/2001 |
| DE | 101 33 305 | 2/2003 |
| FR | 2 649 318 | 1/1991 |
| FR | 2 787 348 | 6/2000 |
| GB | 633 065 | 12/1949 |
| JP | 49 126839 | 12/1974 |
| WO | 91 07943 | 6/1991 |
| WO | 97/27281 | 7/1997 |
| WO | 02/19973 A2 | 3/2002 |

OTHER PUBLICATIONS

Database WPI XP002194121.
Database WPI XP002198062.
WPI Acc No. 1975-38390W/197523 Derwent Abstract of JP 49 126839—1 page (previously submitted).
Database WPI 198201 & JP 56 154408 A to Shiseido Co., Ltd.
The Merck Index, http://themerckindex.cambridgesoft.com/TheMerckIndex/default.asp?formgroup=basenp_form_group&dataaction=db&dbname=TheMerckIndex, 2006.
http://www.snowdriftfarm.com/index.html, "Soapmaking, aromatherapy & spa supplies".
WPI Acc. No. 1975-38390W/197523 Derwent Abstract of JP 49 126839—1 page.
International Search Report No. PCT/EP 03 04366 dated Aug. 29, 2003—2 pp.

*Primary Examiner*—David J Blanchard
*Assistant Examiner*—Rachael E Welter
(74) *Attorney, Agent, or Firm*—Michael P. Aronson

(57) ABSTRACT

A base composition comprising a fatty acid and an organic base to form at least partially a fatty acid organic soap is suitable for preparing a skin care composition by addition of relatively cold water.

18 Claims, No Drawings

METHOD FOR PREPARING A COSMETIC COMPOSITION AND COSMETIC COMPOSITION PREPARED BY THIS METHOD

The invention relates to a method for preparing a cosmetic composition and to the cosmetic composition thus obtained. In particular, it relates to base compositions which may be used in cosmetic compositions such as skin and vanishing creams which may be rapidly prepared, for example, directly by a user. The method of the invention is also suitable for use at larger scale, for example in a factory.

Cosmetic compositions such as skin creams or lotions, and vanishing creams are well known. Such compositions are typically prepared on an industrial scale in a centralised manner, using large-scale equipment. In such a typical production process, for the production of products which are typically emulsions, the highest melting point ingredients are typically heated in a large container until they are molten (typically at around 80° C.), stirred, and further ingredients are added to the composition as it is continually stirred and cooled. The last of these ingredients is often perfume, which may be added when the composition is typically at around 40° C. Thereafter, the composition is cooled and dosed into retail containers. The time and speed of shearing used in the process typically effects the droplet size of the resulting emulsion.

A number of problems may be associated with the common large scale methods of manufacture. Foremost of these is the difficulty of individualisation or customisation of products, with the result that typically only relatively few products may be provided to the consumer. An example of this is the time and cost associated with changing products on a production line; because of the need to thoroughly clean the production apparatus between production runs of different products, especially with large scale manufacturing equipment, this contributes significantly to the difficulties of producing many different products on such a line within a reasonable time scale.

As a consequence of this, where a product is a customised or individualised product, and the batch of that particular product is relatively small, the cost of the product is relatively high.

In addition, a typical skin cream composition may easily comprise 60-90% water. As such, water makes up a large proportion of the weight of a topical product. It therefore represents a large proportion of the cost of transporting such a commercial product between manufacture and retailing. Further more, the cost for heating and cooling the water in the preparation is also high and the processing time is usually long, 3-5 hrs.

Also, in many countries where incomes are relatively low, a consumer often cannot afford to purchase a large container of a cosmetic product. As such, there is high demand for cosmetic compositions which are provided in relatively small dosages, provided these can be made available at relatively low cost.

Yet a further problem associated with topical products is the instability of some of the more desirable ingredients of such products. An example of such an ingredient is retinol. Because retinol is relatively unstable, this leads to the situation where products containing retinol may have a relatively short shelf life, or alternatively a reduction in the functionality of retinol is experienced and accepted during the lifetime of the product. Where topical compositions do contain unstable components, it would be an advantage to be able to prepare them freshly.

U.S. Pat. No. 6,221,346 discloses a powder from which a cream, milk or lotion can be made by addition of water. The powder comprises a specific additive, polyoxyethylene glyceride such as polyoxyethylene oleo-linoleic glyceride. The powder has a particle size of lower than 500 micrometer. We found that those compositions rehydrate only slowly, taking about a few hours at least for (partial) rehydration to take place. The resulting products are generally very thin fluid and do not have the desired viscosity of a cream or lotion. Also they were found to be inhomogeneous.

U.S. Pat. No. 4,753,747 discloses a method for producing a liquid, water soluble aqueous neutralised soap wherein finely divided particles of C10-C22 carboxylic acid are mixed with a neutralizing agent in aqueous medium. The fully neutralised liquid soap that results will form a foam type of product upon rehydration.

We have found a method of manufacturing cosmetic compositions for topical application to the skin (such as, for example, skin creams, lotions, vanishing creams, sun tan lotions, moisturizers, and so on) which particularly lends itself to production of relatively small amounts of such compositions in a short time (eg. a few minutes) whereby there is no need to heat and cool the final compositions, including water, during the preparation. The current method allows a preparation temperature at 0 to 100° C. for preparing a cosmetic composition.

A further advantage of the method we found is that the method enables the preparation of a final product from a base in a short time by the addition of an aqueous composition. Generally the time to obtain a cream or lotion base product from the base according to the invention is from 1 minute to 1 hour.

The fact that the method of the invention may be carried out at any scale and does not require the processing of the base material to a specific particle size is another advantage.

In its broadest aspect, it facilitates the manufacture of a base composition especially in small amounts, which can be readily used to provide all manner of topical skin care compositions. Such a base composition can readily be customised by the addition of suitable active and emotive ingredients, to provide topical skin care compositions as required by the consumer. Such "small scale" production can encompass small industrial scale manufacture by a producer, or re-constitution by a consumer of a small amount of topical product from a concentrate.

The method also facilitates the preparation of a full formulation product at reduced cost because there is no need to heat the water that is included in the formulation at any stage of the preparation process. This saves cost and also saves time needed to prepare the full formulation.

SUMMARY OF THE INVENTION

It has surprisingly been found that a fatty acid organic base soap with a particular degree of neutralisation, either as such in combination with free fatty acid and optionally other surfactants enables the formation of a cosmetic composition when mixing with water at relatively low temperature.

Thus, according to a first aspect the invention relates to a method of providing a topical base composition for use in the preparation of a topical skin care composition, comprising:

(a) providing a mixture comprising fatty acid and an organic base to form at least partially a fatty acid soap wherein the degree of neutralisation of the fatty acid is from 8 to 90%, (b) providing sufficient water based composition at a temperature up to 100° C. such that substantially all of the fatty acid is dispersed or solubilised to provide a base mixture;

(c) optionally further agitating the contents of the composition resulting from step (b);

whereby a topical base composition is formed.

In a second aspect the invention relates to a cosmetic composition obtainable by this method.

In a third aspect the invention relates to an essentially anhydrous composition suitable for the preparation of a cosmetic composition especially a skin cream and to it's use for preparing such cosmetic composition.

In a fourth aspect the invention relates to a kit of parts suitable for preparing a cosmetic composition.

DETAILED DESCRIPTION OF THE INVENTION

The invention provides a method for preparing a topical base composition, preferably a cosmetic composition such as a skin cream. Such compositions include but are not limited to skin creams, lotions, vanishing creams and the like. Preferably the composition can be easily spread on the skin.

In the context of the invention the term topical composition excludes those products wherein the volume fraction of air space, air bubbles and voids is more than 5%.

Hence a preferred composition is characterised by an apparent viscosity of from 0.1 to 10000 Pa·s at a shear rate of $10\ s^{-1}$ to $100\ s^{-1}$ or a yield stress of from 0.1 to 10.000 Pa, preferably from 1 to 10.000 Pa, more preferred from 10 to 1.000 Pa.

A topical base composition such as a cream base or a lotion base, is a base product which in some cases can be used as such but preferably is supplemented with further ingredients to form a full formulation product. A full formulation product is used as a final product and applied by a consumer. The full formulation product is also referred to as final product or more specifically a topical skin care composition.

In the context of the invention a water-based composition is an aqueous medium which mainly comprises water but may also comprise other ingredients. The preferred water based composition is water. Other examples include tea, juices, water with supplemental ingredients such as colouring agent, ingredients with a health benefit, flavour ingredients.

One of the advantages of the method according to the invention is that it enables the use of cold water with a temperature from 0 to 35° C. for the preparation of the base composition. A cosmetic composition generally comprises from 60 to 90 wt % water and hence this provides a saving in energy cost as the large water volumes need not be heated before use. Also if the method is carried out on small scale by a consumer, the consumer need not use hot water and electricity for the preparation which may for example not always be available in low income countries. It is however to be noted that the water based composition can also have a temperature above 35° C. and hence the method according to the invention provides a variety of options.

A (fatty acid) soap is defined as the product resulting from neutralisation reaction between a fatty acid and a base.

In a first step (a) the method provides a mixture comprising fatty acid and an organic base to form at least partially a fatty acid soap.

It is essential for the method according to the invention that the mixture provided in step (a), which is a combination of fatty acid and base results in a partly neutralised fatty acid/soap composition. This means that only part of the fatty acids together with the organic base forms a soap and that there is also free fatty acid left.

Without wishing to be bound by any theory it is believed that the partial neutralisation leads to the formation of a fatty acid soap complexed with free fatty acid. This fatty acid/soap complex swells at ambient temperature on addition of water. The swollen composition is believed to form the basis of the resulting viscous cream or lotion. It was found that compositions which are fully neutralised do not form this fatty acid/soap complex.

The temperature of the water based composition in step (b) is preferably from 0 to 100° C., preferably from 0 to 50° C., more preferred from 0 to 35° C., even more preferred from 0 to 20° C.

This mixing in itself may already be sufficient for the formation of a desired base composition.

Further agitation of the mixture of step (b) is preferred for homogeneity.

Mixing or agitation can be obtained for example by shaking or by simple stirring with a spatula, a spoon or a fork or by using a hand mixer, optionally driven by electricity. Alternatively the mixture is subjected to ultrasound as part of the agitation step.

Conveniently, the mixture is agitated for a period of at least 10 seconds, more preferably at least 20 seconds, even more preferably at least 30 seconds. Conveniently agitation may last up to 5 minutes. Preferably agitation of the mixture is continued until the contents are "set", ie. they do not readily splash around the container during agitation and no particulate is visible.

In a preferred embodiment, the mixture of step (a) is heated to a temperature above the melting temperature of the mixture, preferably in the range of 40° C. to 80° C.; and subsequently cooled to a temperature below the crystallisation temperature of the mixture, preferably below 40° C., more preferred below about 25° C. Said heating is preferably carried out before the water based composition is added. The resulting mixture is preferably made in powder format before water based composition is provided in step (b). The powderisation is especially suitable if further processing is carried out either by an individual consumer or at a different geographic location as where the mixture of step (a) is prepared. Furthermore powderisation is advantageous because enlarges the contact surface between the mixture and the water based composition.

Without wishing to be bound by any theory it is believed that the heating and subsequent cooling of the mixture of step (a) results in the formation of a wax or powder type material which is easy to handle in further processing. The resulting fatty acid soap complex swells in cold water to form a crystal and/or gel phase.

Although in some embodiments of this method the desired soap will form spontaneously upon mixing of the fatty acid and the organic base, in others a heating step is desired or indeed needed for the formation of the soap. Factors that determine whether heating is needed are among others the selected organic base and the hydrocarbon structure of the fatty acid used. It is within the capabilities of a person skilled in the art of cream/lotion manufacture to select the desired combination of free fatty acid and organic base and the preferred heat treatment and conditions thereof, following the guidance provided in this specification and examples.

The mixture of step (a) is at least partially in the form of a fatty acid soap. By controlling the ratio of the fatty acid materials to base, it is possible to control the degree of saponification of the fatty acid materials. This saponification is also referred to as neutralisation. Depending on the ratio of the unneutralised fatty acid materials to soap, and also the amount of water present, it is possible to manipulate the crystal and/or gel phase structure of the resulting mixture, which mixture has been found to be a particularly suitable base material for topical skin compositions.

Base compositions formed according to preferred embodiments of the invention contain in the fatty acid soap material both unneutralized fatty acid material and soap, the ratio of the two being carefully controlled to optimise physical and sensory properties. A base comprising fatty acid soap material which contains too much unneutralised fatty acid material, or too little soap will typically be too hard to spread on the skin, not be in the form of a viscous but flowable cream, and will probably have a grainy feel. However, too much soap or too little fatty acid material in the base composition could produce a composition, which feels too slimey, or a foam.

Preferably in step (a) preferably from 10 to 90%, even more preferably from 10 to 60%, more preferred from 12 to 50%, even more preferred from 15 to 40% of the fatty acids is in the form of an organic base soap.

In step (a) a mixture of free fatty acid and base is prepared. The fatty acid can be any suitable fatty acid, typically containing fatty acid moieties with chain lengths of from $C_{14}$ to $C_{22}$. For the purpose of the invention, "fatty acid" may also include blends of fatty acids. The fatty acid material may also contain relatively pure amounts of one chain length fatty acid moiety. Suitable fatty acids from which fatty acid soaps may be derived include pelargonic, lauric, myristic, palmitic, stearic, isostearic, oleic, linoleic, ricinoleic, arachidic, behenic and erucic acids. Although normally saturated, suitable fatty acid materials may contain unsaturated fatty acid moieties, and may contain fatty acid moieties having a degree of substitution, such as e.g. hydroxy fatty acids.

In certain preferred embodiments, the hydrocarbon chain length of the fatty acid used is from 14 to 22, preferably 14 to 20, more preferably 16 to 18 carbon atoms.

Preferred fatty acids are selected from the group comprising saturated fatty acids or a combination of saturated fatty acids and unsaturated fatty acids.

One of the essential elements in the composition is the organic base. It was found to be essential that the base is an organic base as inorganic base compositions such as potassium or sodium were found to be unsuitable for use in a method where cold water is used to prepare the final skin care composition. The organic base serves to form the above mentioned complex between free fatty acid and fatty acid soap. We have found that the use of a fully neutralized or partly neutralized fatty acid composition wherein the only base is an inorganic base such as sodium hydroxide is not fulfilling the objectives of the invention because such compositions form soaps or acid soap complex that are not soluble in cold water, do not lead to swelling complexes and merely produce foam-type structures. Therefore, although the presence of some amount of inorganic base is tolerable, it is essential that also organic base is present in the method according to the invention.

The organic base is preferably selected from the group comprising triethanolamine, diethanolamine, monoethanolamine, triisopropanalamine, or a combination thereof.

The amount of base added is so as to typically provide partial saponification of the fatty acid thereby generating fatty acid soap material, with it being possible to adjust the rheological properties of the resultant base composition depending on the amount of base added.

To ensure formation of the appropriate crystal structure and avoid premature reaction, it is preferable that the ingredients of the fatty acid soap material be substantially anhydrous prior to the provision of cold water. Once the water has been provided to the mixture, agitation of the water and the fatty acid soap material ingredients is required for homogeneity.

The amount of fatty acid plus fatty acid organic soap is preferably from 70 to 100 wt % on the total weight of the mixture in step (a), and preferably from 0.5 to 30 wt %, more preferred 3 to 20 wt %, more preferably from 5 to 10% on total weight of the cream or lotion base formed.

In one embodiment, optionally the mixture is provided with other surfactants before step (b). Reference is here made to other surfactants because non-neutralised fatty acids are also considered to be surfactants. These other surfactants are preferably not neutralised by the organic base.

Surfactants are common additives in skin creams and lotions. Suitable other surfactants can for example be selected from the group comprising fatty alcohol, fatty acid ester or a combination thereof. Cetylalcohol is an example of a fatty alcohol. Glycerolstearate and glycolstearate are examples of fatty acid esters.

Preferably the mixture of step (a) comprises fatty acid, organic base, cetylalcohol, glycerolstearate and glycolstearate.

Preferably the other surfactant is added in step (a), more preferred before the optional heating to above the melting temperature. Without wishing to be bound by any theory it is believed that the latter mode of addition enables the inclusion of the other surfactants in the crystal and/or gel phase, that forms on hydration, much more quickly.

Preferably the weight ratio of fatty acid soap to other surfactants plus unneutralised fatty acids is from 5:1 to 1:5, most preferred about 1:1.

Compositions obtained by the above described method according to the invention are particularly suited as base materials to provide skin care creams or lotions. In some circumstances, the resultant fatty acid soap material formed after reconstitution with water based composition could provide a suitable topical skin care composition on its own. It is found that other ingredients such as oil, colorant, fragrance, minor ingredients etc. can be added in step (a) and a full formulation product can be made directly. However, it is more desirable to add further ingredients to the composition when mixing with water based composition in step (b) to provide the final skin care composition.

Therefore in a preferred embodiment the base composition is provided with further ingredients preferably selected from the group comprising perfume, preservatives, oil, glycerides, or a combination thereof, optionally before or after step (b), preferably in step (b). To enable customisation of the resulting cosmetic composition, the preferred ingredients are preferably added together with water based composition. Alternatively additional ingredients are added after the base cream or base lotion has been prepared, i.e. after mixing with water based composition in step (b).

In a further aspect the invention relates to a cosmetic composition obtainable by the process according to the invention.

Topical cosmetic compositions according to the invention typically comprise 60-100%, preferably 60 to 99 wt % of aqueous cosmetic base (eg. water, fatty acid and fatty acid base), the balance comprising other components necessary to provide the desired form of topical skin care composition.

Topical cosmetic compositions according to the invention typically have a pH in the region 6 to 9, preferably 6.5 to 8.

Besides water, relatively volatile solvents such as e.g. $C_{1-3}$ monohydric alcohols may be part of the cosmetic vehicle of composition.

Resulting topical compositions according to the invention may typically contain 50% to 90% water, more preferably 70% to 85% water, and sufficient fatty acid, base and/or soap so as to provide a suitable level of fatty acid soap to structure the product. Suitable levels of fatty acid may be in the range 5 to 25%, more preferably 10% to 20%, and soap 0.1 to 10%, more preferably 1% to 4% (if present). The amount of base initially is preferably between 0.1 and 5 wt %.

Emollient materials may also serve as cosmetically acceptable additives. These may be in the form of silicone oils and synthetic esters. Amounts of the emollients may range anywhere from 0.1 to 25%, preferably between 1 and 20% by weight of the final topical skin care composition.

The emollient material may be a silicone oil, an ester or a mixture of these.

Silicone oils may be divided into the volatile and non-volatile variety. The term "volatile" as used herein refers to those materials, which have a measurable vapour pressure at ambient temperature. Volatile silicone oils are preferably chosen from cyclic or linear polydimethyl siloxanes containing from 3 to 9, preferably from 4 to 5 silicon atoms. Linear volatile silicone materials generally have viscosities less than about 5 centistokes at 25° C., whilst cyclic materials typically have viscosities of less than about 10 centistokes.

Non-volatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 25 million centistokes at 25° C. Among the preferred non-volatile silicone emollients useful in the present compositions are the polydimethyl siloxanes having viscosities from about 10 to about 400 centistokes at 25° C.

Among the ester emollients are:
(1) Alkenyl or alkyl esters of fatty acids having 10 to 20 carbon atoms. Examples thereof include isoarachidyl neopentanoate, isononyl isononanoate, oleyl myristate, oleyl stearate, and oleyl oleate.
(2) Ether-esters such as fatty acid esters of ethoxylated fatty alcohols.
(3) Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.
(4) Wax esters such as beeswax, spermaceti, myristyl myristate, stearyl stearate and arachidyl behenate.
(5) Sterol esters of which cholesterol fatty acid esters are examples thereof.

Humectants of the polyhydric alcohol type may also be employed as part of the cosmetic vehicle in skin care compositions of this invention. The humectant aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. The amount of humectant may range anywhere from 0.5 to 30%, preferably between 1 and 15% by weight of the final skin care composition.

Compositions according to the invention may beneficially comprise little or no additional thickener. However, if desired, thickeners (in minor amounts) may also be utilised as part of the cosmetically acceptable vehicle of compositions according to the present invention. Suitable thickeners include cross-linked acrylates (e.g. Carbopol 982), hydrophobically-modified acrylates (e.g. Carbopol 1382), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Alternative thickener is clay. Amounts of the thickener may range from 0.0001 to 2%, usually from 0.001 to 1%, by weight of the composition, if at all.

An oil or oily material may be present, together with an emulsifier to provide typically oil-in-water emulsion, though this will depend largely on the average hydrophilic-lipophilic balance (HLB) of the emulsifier employed.

Various types of additional active ingredients may be present in cosmetic compositions of the present invention. Actives are defined as skin benefit agents other than emollients and other than ingredients that merely improve the physical characteristics of the composition. Although not limited to this category, general examples include additional anti-sebum ingredients such as talcs and silicas, and sunscreens. Further examples include silk protein, fragrances, colouring agents, healthy skin ingredients such as AHA, collagen, amino acids; vitamins such as vitamin A and vitamin E, triple lipids such as lecithin, soy sterol; or combinations thereof.

Sunscreens include those materials commonly employed to block ultraviolet light. Illustrative compounds are the derivatives of PAA, cinnamate and salicylate. For example, azobenzophenone (Parsol 1789®) octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks Parsol MCX and Benzophenone-3 respectively. The exact amount of sunscreen employed in the compositions can vary depending upon the degree of protection desired from the sun's UV radiation.

Many cosmetic compositions, especially those containing water, must be protected against the growth of potentially harmful micro-organisms. Preservatives may therefore be necessary, the need for preservatives may be reduced at low water amounts and/or low pH.

Suitable preservatives include alkyl esters of p-hydroxybenzoic acid, hydantoin derivatives, propionate salts, and a variety of quaternary ammonium compounds. Particularly preferred preservatives of this invention are methyl paraben, propyl paraben, phenoxyethanol and benzyl alcohol. Preservatives will usually be employed in amounts ranging from about 0.1% to 2% by weight of the final skin care composition.

Skin care compositions according to the invention may also include a retinoid. Retinoids increase collagen synthesis by dermal fibroblasts. This results in protection from sun damage and smoothening of wrinkled skin. The term "retinoids" as used herein, includes retinoic acid, retinol, retinal, and retinyl esters. Included in the term "retinoic acid" are 13-cis retinoic acid and all-trans retinoic acid.

The term "retinol" as used herein includes the following isomers of retinol: all-trans-retinol, 13-cis-retinol, 1-cis-retinol, 9-cis-retinol, 3,4-didehydro-retinol. Preferred isomers are all-trans-retinol, 13-cis-retinol, 3,4-didehydro-retinol, 9-cis-retinol. Most preferred is all-trans-retinol, due to its wide commercial activity.

Retinyl ester is an ester of retinol. The term "retinol" has been defined above. Retinyl esters suitable for use in the present invention are $C_1$-$C_{30}$ esters of retinol, preferably $C_2$-$C_{20}$ esters, and most preferably $C_2$, $C_3$, and $C_{16}$ esters because they are more commonly available. Examples of retinyl esters include but are not limited to: retinyl palmitate, retinyl formate, retinyl acetate, retinyl propionate, retinyl butyrate, retinyl valerate, retinyl isovalerate, retinyl hexanoate, retinyl heptanoate, retinyl octanoate, retinyl nonanoate, retinyl decanoate, retinyl undecandate, retinyl laurate, retinyl tridecanoate, retinyl myristate, retinyl pentadecanoate, retinyl heptadecanoate, retinyl stearate, retinyl isosterate, retinyl nonadecanoate, retinyl arachidonate, retinyl behenate, retinyl linoleate, retinyl oleate, retinyl lactate, retinyl glycolate, retinyl hydroxy caprylate, retinyl hydroxy laurate, retinyl tartrate.

If present, the retinoids in the present invention may be present in an amount of from 0.001% to 10%, preferably from 0.01% to 1%, and most preferably from 0.01% to 0.05% by weight of the final skin care composition.

The method according to the invention is especially suitable for preparation of a final, customised cosmetic composition by a consumer. Therefore the mixture in step (a) is preferably provided inside a cosmetic container. The container is preferably such that the final cosmetic composition can be prepared therein. Where the container is used for the preparation of an individual portion of the skin care composition by a consumer, it will preferably be sealed prior to agitation. Such cosmetic containers may preferably have a volume of 20-250 ml, more preferably 25-100 ml, even more preferably 25-50 ml.

Conveniently, the mixture provided in step (a) is a simple mechanical mixture, optionally heated as written above, and may conveniently be in the form of a tablet, powder or amorphous mass. Hence in another embodiment of the invention, there is provided an anhydrous composition in the form of a tablet, powder or amorphous mass for use according to the invention. Such an anhydrous composition may be provided separately in a container in which preparation of the cosmetic base composition occurs. Each unit of anhydrous composition may be individually wrapped.

In a preferred aspect of this embodiment, the invention relates to an essentially anhydrous composition in the form of a tablet, powder or amorphous mass comprising an organic fatty acid soap and fatty acid and optionally other surfactant wherein the amount of fatty acid soap is from 8 to 90% of the total amount of fatty acid plus soap. Preferably the amount of fatty acid soap is at least 12% of the total amount of fatty acid and soap.

In the context of the invention, essentially anhydrous is defined as preferably comprising less than 10 wt % water, preferably less than 5 wt %, more preferred less than 1 wt % water.

The above listed preferred ingredients apply similarly to the essentially anhydrous composition. Especially preferred is that the organic base is selected from the group comprising triethanolamide, monoethanolamide, triisopropanalamine or a combination thereof.

Even more preferred, the fatty acid soap and the unneutralised fatty acid are characterised by a hydrocarbon chain length of from 14 to 20 carbon atoms.

In a further aspect the invention relates to use of said essentially anhydrous composition for preparing a cosmetic composition, preferably a skin cream/lotion. Preferably the skin cream or lotion is prepared within a few minutes.

The mixture or essentially anhydrous composition can be provided to a consumer for individual preparation of a cream in any suitable way. Preferably a kit of parts is provided for preparing a cosmetic composition, said kit comprising a cosmetic container, an essentially anhydrous composition according to the invention and instructions for use of the kit. Said instructions will include guidance on the temperature of the water based composition and amount of water based composition to be added for one unit of anhydrous composition, optional further ingredients that may be added and the desired mode of agitation of the mixture.

Preferably the cosmetic container is provided with measuring signs to show to the consumer the amount of water that is best added to prepare a final cosmetic composition.

To accommodate the desire for customisation, preferably the kit of parts additionally comprises a separate packaging unit comprising a skin cream additive, preferably selected from the group comprising perfume, retinol, colorant, oils, herbs, vitamins or a combination thereof. Alternatively such additive may also be part of the essentially anhydrous composition. According to another embodiment said skin cream additive is mixed with a water based composition which is part of the kit of parts. Said water based composition optionally comprises (part of) the additives.

The invention is now illustrated by the following non limiting examples.

EXAMPLES

The following tables include the anhydrous ingredients, which are prepared in step (a). Water and other ingredients added in step (b) are listed out side the table.

Example 1

All ingredients of table I were mixed and melted at 80° C. Subsequently the mixture was cooled to about 20° C. and then made into a powder.

The degree of neutralisation was 14.8%

Water of room temperature was added and the resulting composition was mixed for about 1-2 minutes with a spatula.

A smooth, homogeneous skin cream resulted.

TABLE 1

| Ingredients | W/W % of the topical composition |
| --- | --- |
| Glycerine | 1 |
| Stearic acid | 18.0 |
| Cetyl alcohol | 0.5 |
| Triethanolamine | 1.4 |
| Octyl methoxy cinnamate | 1.0 |
| Butyl methoxy dibenzoyl | 0.5 |
| Dimethicone | 0.2 |
| Niacinamide | 1 |
| Tetra sodium EDTA | Trace |
| Methyl paraben | 0.1 |
| Propyl paraben | 0.1 |
| Phenoxy ethanol | 0.4 |
| Perfume | 0.5 |
| Water | 75.3 |

Example 2

TABLE 2

| Ingredients | W/W % of the topical composition |
|---|---|
| Stearic acid | 18.0 |
| Triethanolamine | 1.6 |
| Water | 80.4 |

The procedure of example 1 was used.

The degree of neutralisation was 16.9%

The resulting product is a smooth, homogeneous base composition, which can either be used directly or may be supplemented with common ingredients to prepare the final skin cream.

Example 3

TABLE 3

| Ingredients | W/W % of the topical composition |
|---|---|
| Glycerine | 3 |
| Stearic acid | 2.6 |
| Cetyl alcohol | 0.4 |
| Triethanolamine | 0.8 |
| Glycol stearate | 1.4 |
| $TiO_2$ | 0.1 |
| Fragrance | 0.2 |
| Yellow colour | 0.01 |
| Glycerol stearate | 0.6 |
| Dimethicone | 0.2 |
| Mineral oil | 3 |
| Water | 87.7 |

The procedure of example 1 was used.

The degree of neutralisation was 58.6%

A smooth, homogeneous skin cream resulted.

Example 4

TABLE 4

| Ingredients | W/W % of the topical composition |
|---|---|
| Stearic acid | 2.6 |
| Cetyl alcohol | 0.4 |
| Triethanolamine | 0.8 |
| Glycerol stearate | 0.6 |
| Glycol stearate | 1.4 |
| Silicon oil | 0.5 |
| Sun flower oil | 3 |
| Fragrance | 0.1 |
| Red colorant | 0.01 |
| Water | 90.6 |

Procedure

All ingredients of table 4 were mixed and melted at 80° C. Subsequently the mixture was cooled to about 20° C. and then made into a powder. The degree of neutralisation was 58.6% Water of room temperature was added and simultaneously the silicon oil, sunflower oil, fragrance and red colorant were mixed in. The resulting composition was mixed for about 2 minutes with a spatula.

Example 5

| Ingredients | W/W % of the topical composition |
|---|---|
| Stearic acid | 20 |
| Triethanolamine | 0.84 |
| Water | 79.2 |

The procedure of example 1 was used.

The degree of neutralisation was 8%

The resulting product is a smooth, homogeneous base composition, which can either be used directly or may be supplemented with common ingredients to prepare the final skin cream.

Example 6

Diethanolamine as base material. The composition was as follows:

TABLE

| Ingredients | W/W % of the topical composition |
|---|---|
| Diethanol amine | 1.0 |
| Stearic acid | 15 |
| Water | 84 |

The procedure of example 1 was used.

The degree of neutralisation was 18.6%

A smooth, homogeneous skin cream resulted.

The invention claimed is:

1. A method of providing a topical base composition for use in the preparation of a skin cream, a skin lotion or a vanishing cream containing 50 to 90% water, the said method comprising:
    (a) providing an essentially anhydrous mixture comprising fatty acid and an organic base wherein said mixture is heated to a temperature in the range of 40° C. to 80° C. to form, at least partially, a fatty acid soap wherein a degree of neutralisation of the fatty acid is from 8 to 90%, and wherein the mixture is subsequently cooled to a temperature below the crystallization temperature before a water based composition is added in step (b),
    (b) providing sufficient water based composition at a temperature up to 100° C. such that all of the fatty acid is dispersed or solubilised to provide a base mixture;
    (c) optionally further agitating the contents of the composition resulting from step (b); whereby a topical base composition is formed.

2. A method according to claim 1 wherein the hydrocarbon chain length of the fatty acid is from 14-20 carbon atoms.

3. A method according to claim 1 wherein the water based composition is water.

4. A method according to claim 1 wherein the temperature of the water based composition is from 0 to 70° C.

5. A method according to claim 1 wherein the organic base is selected from the group comprising triethanolamine, monoethanolamine, triisopropanalamine, diethanolamine, or a combination thereof.

6. A method according to claim 1 wherein the mixture of step (a) is provided with surfactant selected from the group consisting of fatty alcohol, fatty acid ester or a combination thereof.

7. A method according to claim 6 wherein the surfactant is added in step (a) before heating to a temperature in the rancge of 40° C. to 80° C.

8. A method according to claim 1 wherein the amount of fatty acid plus fatty acid organic soap is from 50 to 100 wt % based on the total weight of the mixture in step (a).

9. A method according to claim 1 wherein the weight ratio of fatty acid soap to unneutralised fatty acid plus other surfactants that may be present, is from 5:1 to 1:5.

10. A method according to claim 1 wherein the mixture is provided with further ingredients selected from the group consisting of perfume, preservatives, oil, glycerides, or a combination thereof in step (a) or (b).

11. A method according to claim 1 wherein the mixture in step (a) is provided inside a cosmetic container.

12. A method according to claim 1 wherein the mixture of step (a) contains less than 5% water; wherein the topical base composition has a volume fraction of air space, air bubbles and voids that is less than or equal to 5%; and wherein the topical base composition is a skin cream, a skin lotion or a vanishing cream.

13. A method according to claim 1 wherein the mixture recited in step (a) is cooled to a temperature below 25° C.

14. A method according to claim 1 wherein the water based composition is at a temperature of 0° C. to 50° C.

15. A method according to claim 1 wherein the water based composition is at a temperature of 0° C. to 35° C.

16. A method according to claim 1 wherein the mixture recited in step (a) does not contain an inorganic base.

17. A method according to claim 1 wherein the mixture recited in step (a) does not contain an inorganic base and wherein the topical base composition consists of fatty acid; fatty acid soap; optional surfactant selected from the group consisting of fatty alcohol, fatty acid ester and a combination thereof; and optional further ingredients selected from the group consisting of perfume, preservatives, oil, glycerides, and a combination thereof.

18. A method according to claim 1 wherein the mixture recited in step (a) is cooled to a temperature below 40° C.

* * * * *